(12) United States Patent (10) Patent No.: US 9,730,627 B2
Andrisani (45) Date of Patent: Aug. 15, 2017

(54) MUSCLE FATIGUE MEASURING DEVICE AND ASSOCIATED SYSTEMS AND METHODS

(71) Applicant: Damian Andrisani, Newark, DE (US)

(72) Inventor: Damian Andrisani, Newark, DE (US)

( * ) Notice: Subject to any disclaimer, the term of this patent is extended or adjusted under 35 U.S.C. 154(b) by 328 days.

(21) Appl. No.: 14/549,986

(22) Filed: Nov. 21, 2014

(65) Prior Publication Data

US 2015/0141872 A1 May 21, 2015

Related U.S. Application Data

(60) Provisional application No. 61/907,106, filed on Nov. 21, 2013.

(51) Int. Cl.
*A61B 5/22* (2006.01)
*A61B 5/00* (2006.01)

(52) U.S. Cl.
CPC .............. *A61B 5/225* (2013.01); *A61B 5/706* (2013.01); *A61B 5/743* (2013.01); *A61B 5/7475* (2013.01)

(58) Field of Classification Search
CPC .... A61B 5/255; A61B 5/706; A63B 23/03508
USPC ............................................ 600/587; 33/512
See application file for complete search history.

(56) References Cited

U.S. PATENT DOCUMENTS

| | | | |
|---|---|---|---|
| 2,680,967 A | 6/1954 | Newman | |
| 3,465,592 A * | 9/1969 | Perrine .................. | A61B 5/224 482/113 |
| 3,680,386 A | 8/1972 | Cannon | |
| 4,607,841 A * | 8/1986 | Gala ..................... | A63B 21/002 482/91 |
| 4,886,073 A | 12/1989 | Dillon et al. | |
| 5,090,421 A | 2/1992 | Wagoner, III | |
| 5,184,628 A * | 2/1993 | Shah ...................... | A61B 5/225 600/587 |
| 5,518,470 A * | 5/1996 | Piaget .................. | A63B 22/001 482/51 |
| 5,788,608 A * | 8/1998 | Wilkinson ......... | A63B 21/0724 482/51 |
| 5,800,310 A * | 9/1998 | Jones ................. | A63B 21/0615 482/100 |
| 5,911,695 A | 6/1999 | Watkins et al. | |
| 6,100,287 A * | 8/2000 | Stevens ................ | A61K 31/195 514/400 |
| 6,227,047 B1 * | 5/2001 | Livingston ............. | A61B 5/224 73/379.08 |
| 6,572,567 B1 * | 6/2003 | Carroll ................... | A61B 5/224 600/587 |

(Continued)

FOREIGN PATENT DOCUMENTS

WO     WO 9305711 A1 *  4/1993   ........... A61B 5/1036

*Primary Examiner* — Michael C Stout
(74) *Attorney, Agent, or Firm* — McCarter & English, LLP

(57) ABSTRACT

Exemplary embodiments are directed to muscle fatigue measuring devices that include a bottom stabilizing portion, a handle, a central extended portion, and a force measuring device. The central extended portion can be disposed between the bottom stabilizing portion and the handle. The force measuring device can be connected to the handle. The force measuring device can be adapted to measure a force applied to the handle. Exemplary embodiments are also directed to methods of measuring muscle fatigue and muscle fatigue measuring systems.

20 Claims, 11 Drawing Sheets

(56) References Cited

U.S. PATENT DOCUMENTS

| | | | |
|---|---|---|---|
| 7,608,025 B1* | 10/2009 | Best | A63B 21/0023 482/123 |
| 2004/0082877 A1* | 4/2004 | Kouou | A61B 5/0488 600/546 |
| 2007/0129224 A1* | 6/2007 | Karafa | A63B 21/055 482/123 |
| 2008/0051263 A1* | 2/2008 | Rasmussen | A63B 21/156 482/94 |
| 2008/0119763 A1* | 5/2008 | Wiener | A61B 5/224 600/587 |
| 2009/0048074 A1* | 2/2009 | Kamins | A61B 5/1071 482/52 |
| 2012/0184871 A1* | 7/2012 | Jang | A61B 5/221 600/546 |
| 2012/0220428 A1* | 8/2012 | Carlson | A63B 21/4003 482/8 |

\* cited by examiner

MUSCLE FATIGUE MEASURING DEVICE AND ASSOCIATED SYSTEMS AND METHODS

CROSS-REFERENCE TO RELATED APPLICATIONS

The present application claims the benefit of a provisional patent application entitled "Muscle Fatigue Measuring Device" which was filed on Nov. 21, 2013, and assigned Ser. No. 61/907,106. The entire content of the foregoing provisional application is incorporated herein by reference.

TECHNICAL FIELD

The present disclosure relates to muscle fatigue measuring devices and associated systems and methods and, in particular, to devices which measure the strength and fatigue of a person's arm and/or shoulder muscle(s), thereby allowing monitoring of the arm and/or shoulder muscle(s) to anticipate and prevent injury.

BACKGROUND

Arm and shoulder muscles are used to perform many tasks, including every day activities and while playing sports. These tasks often require the person to possess adequate muscle strength to perform the tasks properly or to avoid injury. In addition, for medical rehabilitation purposes, the patient is generally required to reach a certain muscle strength level prior to performing tasks with a recovering arm.

As an example, in the case of a baseball player, the player is required to have sufficient muscle strength to throw a ball at a certain speed and location. For a pitcher, the ball must also be thrown repetitively. Similarly, as a further example, a worker may be required to perform a job that involves extending his arm out in front of his body, e.g., swinging a hammer, typing, sweeping, or the like. The job may also involve repetitive motion.

To perform these tasks properly, avoid overuse, and avoid potential injury, the arm and shoulder muscles must have adequate strength. A pitcher without adequate muscle strength may not be able to consistently throw a ball at a certain speed and location. The pitcher may also be at a heightened risk of injury. Similarly, a worker without adequate muscle strength may incorrectly perform a task or potentially suffer injury. As muscles fatigue, the person must work the muscles harder in order to meet the requirements of the task at hand. Such added exertion can lead to injury, such as structural or ligament damage to the arm or shoulder. These injuries may be chronic or even debilitating.

Thus, a need exists for devices and methods for testing and monitoring muscle fatigue in a person involved in executing tasks or undergoing rehabilitation such that injury can be anticipated, reduced or prevented. These and other needs are addressed by the devices, systems and methods of the present disclosure.

SUMMARY

In accordance with embodiments of the present disclosure, a muscle fatigue measuring device is provided for testing, measuring and monitoring the strength and fatigue of a person's arm and/or shoulder muscles to prevent or reduce injury. The device includes a bottom stabilizing portion, a handle and a central extended portion. In some embodiments, the bottom stabilizing portion can be, e.g., a base, a support, a stabilizing member, or the like. In some embodiments, the central extended portion can be, e.g., a post, a connecting member, a support, a stand, or the like. In some embodiments, the bottom stabilizing portion and the central extended portion can be separately formed and connected relative to each other. In some embodiments, the bottom stabilizing portion and the central extended portion can be integrally formed, e.g., constructed from a single piece of material. The central extended portion can be disposed between the bottom stabilizing portion and the handle. The device includes a force measuring device connected to the handle, e.g., electronically connected, physically connected, or both. The force measuring device can be adapted to measure a force applied to the handle.

The bottom stabilizing portion can be adapted to be positioned on a supporting surface, e.g., a floor. In some embodiments, the bottom stabilizing portion can include a flat bottom plate adapted to be positioned on the supporting surface. In some embodiments, the bottom stabilizing portion can include a distance measuring device attached thereto.

A height of the central extended portion can be adjustable. In some embodiments, the post can include a first section, e.g., a first post, concentrically positioned within a second section, e.g., a second post, in a telescoping manner. The first section can include a spring-loaded push button. The second section can include a plurality of apertures configured to receive the spring-loaded push button.

In some embodiments, the force measuring device can be a load cell. The force measuring device can be disposed between the handle and a proximal end of the central extended portion. The force measured by the force measuring device can be an upwardly directed force away from the bottom stabilizing portion and the central extended portion.

In some embodiments, the device can include a processing device and a graphical user interface secured to at least one of the handle, the central extended portion, or the bottom stabilizing portion. The graphical user interface can display the force applied to the handle and measured by the force measuring device.

In accordance with embodiments of the present disclosure, an exemplary method of measuring muscle fatigue is provided. The method includes providing the muscle fatigue measuring device described herein. The method includes grasping the handle and applying a force to the handle. The method further includes measuring the force applied to the handle with the force measuring device. Grasping the handle and applying a force to the handle can include applying an upwardly directed force on the handle.

In some embodiments, the method can include comparing the measured force with a baseline force value to determine if muscle fatigue is occurring. In some embodiments, the method includes determining whether the measured force is below a percentage of a baseline force value to determine if muscle fatigue is occurring. In some embodiments, the method includes determining whether the measured force is within a predetermined range of force values that signals muscle fatigue.

In accordance with embodiments of the present disclosure, an exemplary muscle fatigue measuring system is provided. The system includes a muscle fatigue measuring device as described herein. The system further includes a processing device connected to the force measuring device of the muscle fatigue measuring device. The processing device can be adapted to display the measured force. The processing device can include a graphical user interface for displaying the measured force.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed devices and associated systems and methods, reference is made to the accompanying figures, wherein.

DESCRIPTION OF EXEMPLARY EMBODIMENTS

In accordance with embodiments of the present disclosure, an exemplary muscle fatigue measuring device is provided. The exemplary device can be used to measure the fatigue in certain muscles such that injury to the muscles can be prevented or anticipated. Although discussed herein with respect to a baseball pitching motion, it should be understood that the devices discussed herein can be used for measuring muscle fatigue in a variety of tasks. For example, the devices can be used to measure muscle fatigue related to sports, physical labor, medical rehabilitation, combinations thereof, or the like.

Figure 1:
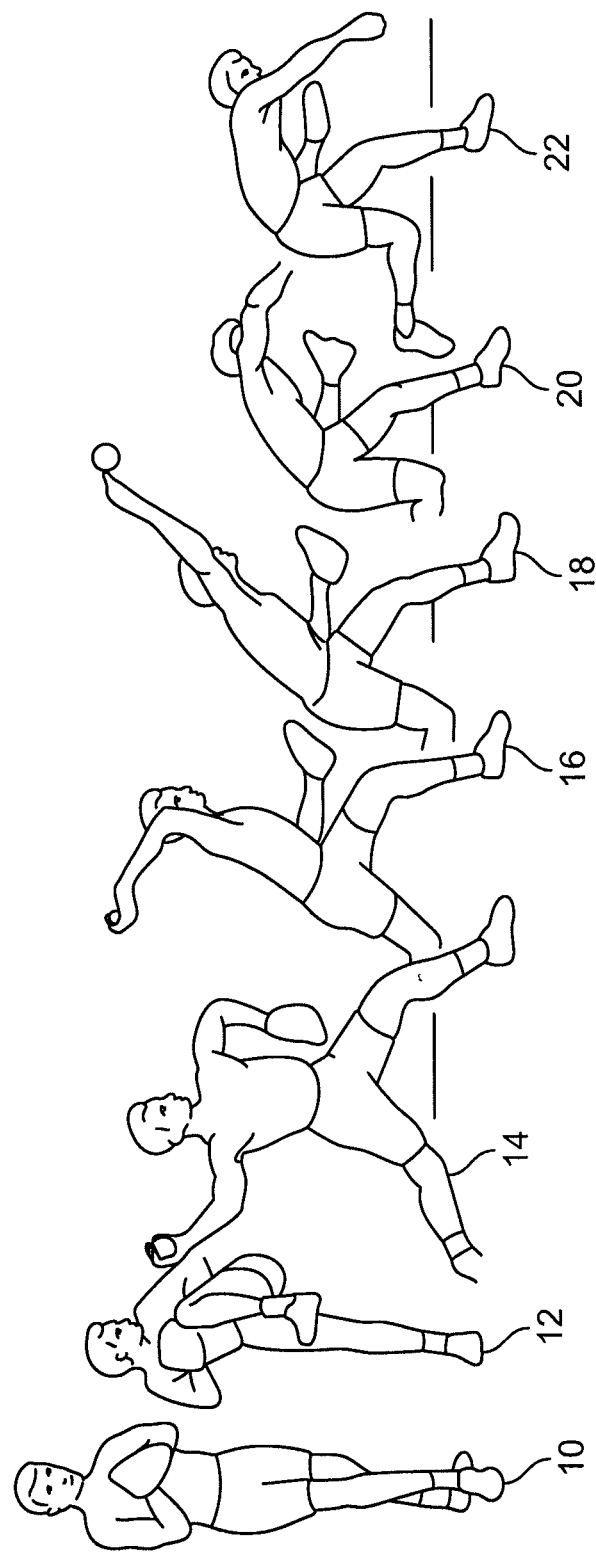
FIG. 1 is a diagrammatic view of phases of a pitching motion.

With respect to FIG. 1, a diagrammatic illustration is provided of phases of a pitching motion. In particular, the first phase 10 represents the wind-up. The second phase 12 represents the knee in an upward position. The third phase 14 represents the stride, foot contact, and arm cocking. The fourth phase 16 represents the maximum external rotation and arm acceleration. The fifth phase 18 represents the release and arm deceleration. The sixth phase 20 represents the maximum internal rotation. The seventh phase 22 represents the follow-through.

Using electromyography (EMG), previous studies have established which muscles are utilized in different phases of the throwing motion of a baseball pitcher. Based on these studies, it was determined that the muscles used to decelerate the arm after the ball is released (e.g., the fifth phase 18) are the trapezius, infraspinatus, teres minor, serratus anterior, and biceps. (See, e.g., Gowan, I. D. et al., *A comparative electromyographic analysis of the shoulder during pitching: professional versus amateur pitchers*, Am. J. Sports Med., 15:6, p. 586-590, (1987); and Jobe, F. W. et al., *An EMG analysis of the shoulder in pitching: a second report*, Am. J. Sports Med., 12:3, p. 218-220 (1984)). In particular, the deceleration phase of the throwing motion utilizes these muscles to resist internal rotation of the shoulder.

While these muscles provide a dynamic restraint, the posterior capsule provides a static restraint if the internal rotation force exceeds the muscular capabilities. The failure load of the capsule is between approximately 800 Newtons and 1200 Newtons in young individuals. (See, e.g., Reeves, B., *Experiments on the tensile strength of the anterior capsular structures in man*, J. Bone Joint Surg. Br., 50(4), p. 858-865 (1968)). At the time of ball release, distraction forces in the shoulder approximate 950 Newtons. (See, e.g., Braun, S. D. et al., *Shoulder injuries in the throwing athlete*, J. Bone Joint Surg. Am., 91(4), p. 966-978 (2009)). Studies have demonstrated that the decelerating muscles fatigue and neuromuscular activation deficits can develop. (See, e.g., Gandhi, J. et al., *Voluntary activation deficits of the infraspinatus present as a consequence of pitching-induced fatigue*, J. Shoulder Elbow Surg., 21, p. 625-630 (2012); and Bowman, T. G. et al., *A functional fatiguing protocol and deceleration time of the shoulder from an internal rotation perturbation*, J. Athl. Train., 41(3), p. 275-279 (2006)). It is believed that the muscle fatigue and neuromuscular activation deficits contribute to many of the overuse injuries that pitchers develop, particularly posterior capsule contractures and thickening, glenohumeral internal rotation deficits (GIRD), superior anterior to posterior labral (SLAP) tears, rotator cuff tears, biceps tendinosis, and ulnar collateral ligament injuries.

In an effort to identify when these muscles are fatigued during a game, prior to the development of a pathologic cascade that leads to injury, the muscle fatigue measuring device discussed herein can be used. In order to establish the optimal position of muscle testing to mirror the deceleration phase of throwing, a fine wire EMG study was performed. The study determined the degree of activation of the supraspinatus, infraspinatus, and teres minor muscles. A baseline activation level was obtained for each muscle by performing maximum isometric external rotation testing at approximately 0 degrees, 45 degrees and 90 degrees of shoulder abduction, and empty can testing. These studies established the maximum voluntary contraction (MVC) for each muscle.

Isometric testing was performed in the follow through position for a pitcher with the throwing hand at roughly waist height, e.g., an approximately 45 degree angle. The Konigsberg Electromyography (EMG) telemetry unit (Konigsberg Instruments, Pasadena, Calif.) was used to measure myoelectric activity that was detected by custom made fine wire electrodes. A single ended amplifier (impedance >10 MΩ) was used with a 4th order Butterworth filter (20 to 500 Hz) and a common mode rejection ratio (CMRR)

of 130 db at DC (minimum 85 db across an entire frequency of 10 to 500 Hz). The signal was converted from analog to digital data with an A/D card (Keithley Metrabyte DAS-1000, Keithley Instruments Inc., Tauton, Mass.), passed to a computer where raw EMG data was sampled at a frequency of approximately 2,000 Hz, and further analyzed with Lab-VIEW® software (National Instruments, Austin, Tx).

Intramuscular fine wire bipolar electrodes were placed into the supraspinatus, infraspinatus, and teres minor under sterile conditions using a single-needle technique. (See, e.g., Basmajian, J. V. et al., *Muscles alive: Their functions revealed by electromythography*, 5$^{th}$ ed., Baltimore: Williams & Wilkins (1985)). Following skin cleansing with Betadine, dual 0.002-inch diameter, Stablohm 800 A stainless steel wires insulated with heavy-poly nylon (California Fine Wire Co., Grover, Calif.) were inserted into the muscle with a 25-gauge hypodermic needle. Since minimal pain is experienced during the indwelling electrode procedure, anesthesia was not necessary.

The methods of electrode placement for the supraspinatus, infraspinatus, and teres minor followed previous studies performed in the industry. (See, e.g., Perotto, A. O., *Anatomical Guide for the Electromyographer: The Limbs and Trunk*, Springfield, Ill. 62704, Charles C. Thomas Publisher (2005)). After the electrodes were placed in the muscle tissue, the hypodermic needle was removed and discarded. The subject performed repeated muscle contractions to embed the electrode in the muscle's contractile tissue. The protruding ends of the electrode were taped to the skin to avoid accidental withdrawal during testing. The exposed bared ends were attached to connector cables and completed the circuit by connecting the electrode/wires to an amplifier. Correct placement of all electrodes was confirmed by monitoring myoelectric activity during isolated muscle testing of the specific muscle.

After correct placement was confirmed, the subject performed a Maximum Voluntary Isometric Contraction (MVIC) for each muscle to use for EMG normalization. Following the MVIC for each muscle, the subject completed three trials of pulling against a custom made torque/position measuring instrument at four different angles (e.g., approximately 35 degrees, 45 degrees, 55 degrees, and 35 degrees with subject having to reach lower to grab the handle). These positions were chosen based on the biomechanics of throwing and designed to simulate eccentric contractions after a pitcher releases a ball.

EMG data collected during the trials was filtered with a phase corrected fourth order Butterworth band pass filter. The lower cutoff frequency was approximately 20 Hz and the upper frequency was approximately 500 Hz. (See, e.g., Merletti, R. et al., *Modeling of Surface Myoelectric Signals—Part I: Model Implementation*, IEEE Transactions on Biomedical Engineering, Vol. 46, No. 7, p. 810-820, ISSN 0018-9294 (1999)). After application of the filter, data was rectified and smoothed using a 25 ms root-mean-square (RMS) linear envelope. The custom LabVIEW® program was able to select the middle one second of the contraction period, which was used for analysis. The EMG data from the trials using the custom made device were further normalized to the EMG values of the MVIC's for each muscle to indicate a value as a percentage of MVIC. The EMG data during each condition were averaged across three separate trials. The resulting data is displayed in Table 1 below.

TABLE 1

Muscle Activation As Compared To MVIC

| Trial | Torque | Supraspinatus | Infraspinatus | Teres Minor |
|---|---|---|---|---|
| 35 Degrees | 806 | 110% | 51% | 88% |
| 45 Degrees | 781 | 107% | 63% | 71% |
| 55 Degrees | 879 | 116% | 27% | 99% |
| 35 Degrees Reaching Low | 1076 | 109% | 59% | 89% |

Based on the experimentation described above, the supraspinatus activation was measured to be approximately 107% of MVC, the infraspinatus activation was approximately 63% of MVC, and the teres minor activation was approximately 71% of MVC. The data in Table 1 established that the supraspinatus, infraspinatus, and teres minor muscle group is active in producing a force in the above described deceleration during the pitching motion (or similar motions during alternative tasks). The loss of strength during the deceleration phase of the pitching motion due to muscle fatigue or activation deficits can develop over the course of pitching during a baseball game. The muscle fatigue measuring device of the present disclosure allows, for example, athletes, patients undergoing physical therapy, or the like, to monitor and determine the fatigue and/or development of the supraspinatus, infraspinatus, and teres minor muscles over time. By monitoring fatigue associated with the specific muscles being used during the measured motions, preventative measures can be taken prior to muscle injury due to fatigue.

The disclosed muscle fatigue measuring device can be used for quantitatively testing and measuring the strength of a person's arm and/or shoulder muscle(s). The muscle fatigue measuring device can be used statically (e.g. once) or can be used dynamically over a period of time to establish a reference muscle strength point, or fatigue point. The muscle fatigue measuring device can be used to determine changes in muscle strength or when the muscles have reached a predetermined level of fatigue, such as, for example, the point where continued muscle use may compromise effectiveness and result in injury.

For example, for purposes of measuring muscle fatigue of a pitcher during a baseball game, the muscle fatigue measuring device can be used to measure the initial muscle strength of the pitcher and further measurements can be taken in between innings to determine the reduction in muscle strength caused by muscle fatigue. Upon reaching a predetermined fatigue point, the pitcher can be rested to prevent injury to the arm and/or shoulder muscle(s). As a further example, for purposes of rehabilitation, the muscle fatigue measuring device can be used to measure the initial muscle strength of the patient post-surgery, and further measurements can be taken throughout the rehabilitation process until the patient reaches a strength representative of a healed arm and/or shoulder capable of performing day-to-day tasks. As yet a further example, for purposes of rehabilitation, a reference value based on average arm and/or shoulder muscle strength can be used to determine if the arm and/or shoulder muscle(s) of the patient have healed post-surgery.

The exemplary muscle fatigue measuring devices described herein generally include a handle, a bottom stabilizing portion, and a central extended portion disposed between the bottom stabilizing portion and the handle. In some embodiments, the bottom stabilizing portion can be, e.g., a base, a support, a stabilizing member, or the like. In some embodiments, the central extended portion can be, e.g., a post, a connecting member, a support, a stand, or the like. In some embodiments, the bottom stabilizing portion and the central extended portion can be separately formed and connected relative to each other. In some embodiments, the bottom stabilizing portion and the central extended portion can be integrally formed, e.g., constructed from a single piece of material.

With reference to FIGS. 2-5, perspective, side and detailed views of an exemplary muscle fatigue measuring device 100 are provided. The device 100 includes a handle section 102, a base section 104 (e.g., a bottom stabilizing portion), and a post section 106 (e.g., a central extended portion) connecting the handle section 102 and the base section 104. In particular, the handle section 102 and the base section 104 can be connected to opposing ends of the post section 106. The handle section 102 can include a bracket 108 bolted or secured to the post section 106. The bracket 108 includes two opposing diagonal members 110 extending upwardly from the post section 106 and two opposing vertical members 112 extending upwardly from the ends of the diagonal members 110.

The handle section 102 can include a shaft 114, e.g., a bar, extending between the vertical members 112. The shaft 114 and the distance between the vertical members 112 can be configured and dimensioned to receive a grip 116. In particular, the grip 116 can be disposed between the vertical members 112 and the shaft 114 can be passed through an aperture formed in the grip 116. In some embodiments, the grip 116 can be fixedly secured between the vertical members 112 and on the shaft 114. In some embodiments, the grip 116 can be rotatably secured on the shaft 114 such that the grip 116 can rotate about the shaft 114. In some embodiments, the handle section 102 can include one or more spacers 118 positioned between the grip 116 and the vertical members 112.

The grip 116 of the handle section 102 can be grasped by the person whose muscle strength or fatigue is to be measured. The grip 116 can be configured and dimensioned to be held in the hand of the user. For example, the space between the diagonal members 110 and the vertical members 112 can form an arch and be dimensioned to permit passage of fingers therethrough such that the fingers can wrap around and grasp the grip 116. The grip 116 can be designed to be held in either one hand or two hands. The size of the grip 116 can be designed to accommodate a variety of hand sizes. The width of the grip 116 can be between approximately 4 inches and approximately 30 inches. The circumference of the grip 116 can be between approximately 1 inch and approximately 6 inches.

The handle section 102 and the grip 116 can be fabricated using any material known to one skilled in the art to make a grip 116. For example, the handle section 102, grip 116, or both, can be fabricated from, e.g., metal, polymer, composite, combinations thereof, or the like. In some embodiments, the grip 116 can include padding, e.g., foam padding, positioned thereon to at least partially cover the grip 116, thereby providing comfort to the user. The handle section 102 can be designed to support a force of at least approximately 200 lbs.

The base section 104 can include two diagonal members 120 extending in opposing directions from the post section 106 and two vertical members 122 extending from the diagonal members 120. In some embodiments, the diagonal members 120 and the vertical members 122 can define a substantially flat, planar configuration. The base section 104 further includes a bottom plate 124, e.g., a rectangular planar plate, secured to the vertical members 122. In some embodiments, the base section 104 can be fixedly secured to a distal end of the post section 106 opposing the proximal end of the post section 106 at which the handle section 102 is attached. In some embodiments, the base section 104 can be integrally formed with the post section 106, e.g., fabricated from a single piece of material. The bottom plate 124 can be configured and dimensioned to be positioned on a flat surface, e.g., a floor, during use of the device 100.

In some embodiments, the width of the bottom plate 124 can be substantially similar to the width of the diagonal members 120 and the vertical members 122. In some embodiments, the bottom plate 124 can be dimensioned to extend anteriorly and posteriorly relative to the vertical members 122 (see, e.g., FIGS. 2, 3 and 5). Extension of the bottom plate 124 from the vertical members 122 can assist in stabilizing the device 100 during use or storage. The assembly of the diagonal members 120, the vertical members 122, and the bottom plate 124 can form a stirrup or arch-shaped passage 126 therebetween. The passage 126 can be configured and dimensioned to receive a foot of a user at least partially therethrough.

In some embodiments, the base section 104 can include a distance measuring device 128, e.g., measuring tape, a digital measuring device, or the like, attached thereto. As will be discussed in greater detail below, the measuring device 128 can be used to measure the stride of the user during a pitching motion as shown in phase three 14 of FIG. 1. For example, the measuring device 128 can be secured to one of the vertical members 122. In some embodiments, rather than a fixedly secured measuring device 128, a measuring device 128 can be detached from the base section 104 or a measuring device 128 not associated with the device 100 can be used to measure the stride of the user.

During use, the user can place the leading foot during the pitching stride within the passage 126 and on top of the bottom plate 124. The weight of the user and the pressure of the foot on the bottom plate 124 can therefore maintain the device 100 secured to the floor during use. In some embodiments, the base section 104 can include means for securing the bottom plate 124 during use of the device 100. In particular, because a lifting force is applied to the device 100 at the handle section 102, the base section 104 can be designed to be secured to the ground or a heavier object such that the base section 104 will not move during use of the device 100.

The base section 104 can be fabricated from any material(s) known to those of ordinary skill in the art. For example, the base section 104 can be fabricated from, e.g., a metal, a polymer, a composite, combinations thereof, or the like. In some embodiments, the base section 104 can be fabricated from materials having a sufficient weight to counter the lifting force on the handle section 102. In some embodiments, the base section 104 can be designed to support a force of at least approximately 200 lbs.

Figure 2:
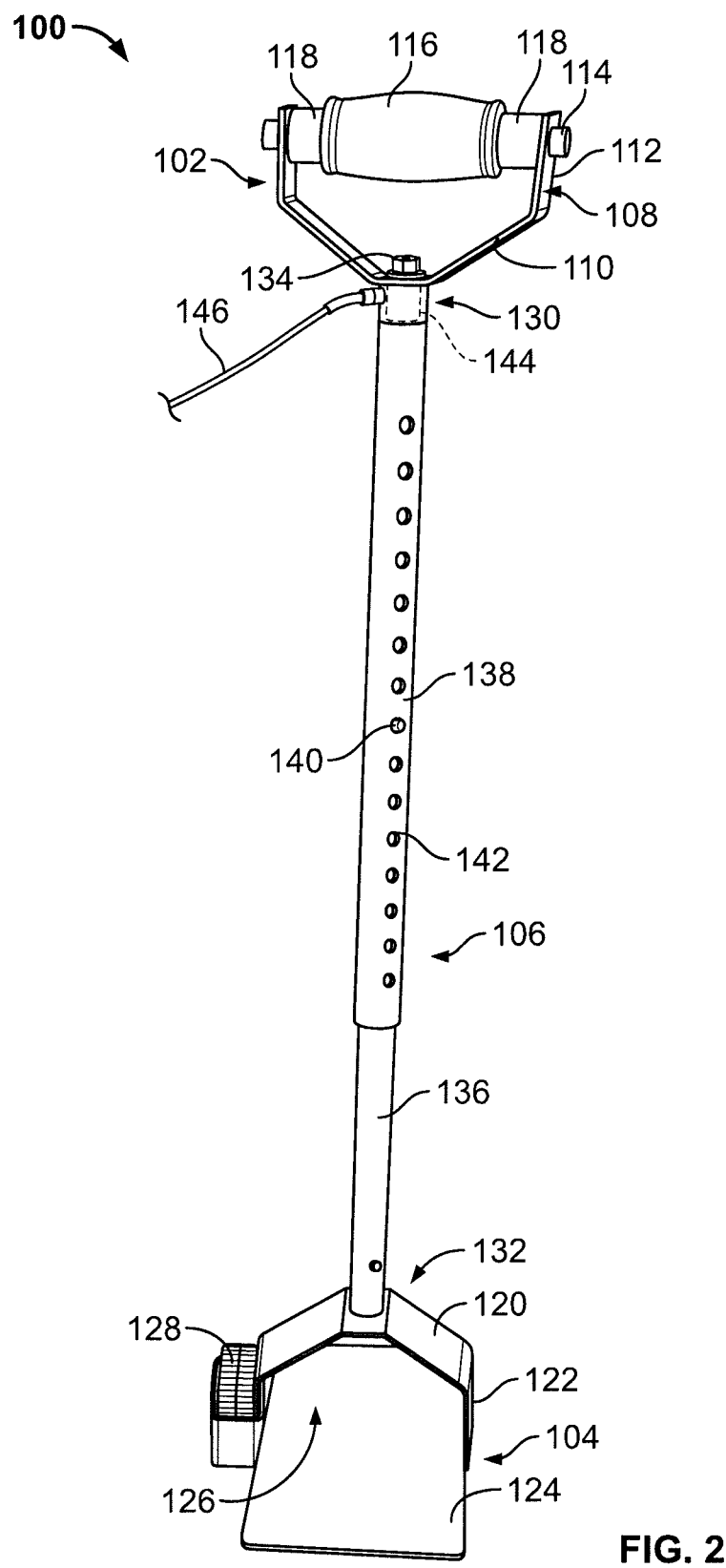
FIG. 2 is a perspective view of an exemplary muscle fatigue measuring device according to the present disclosure.
Figure 3:
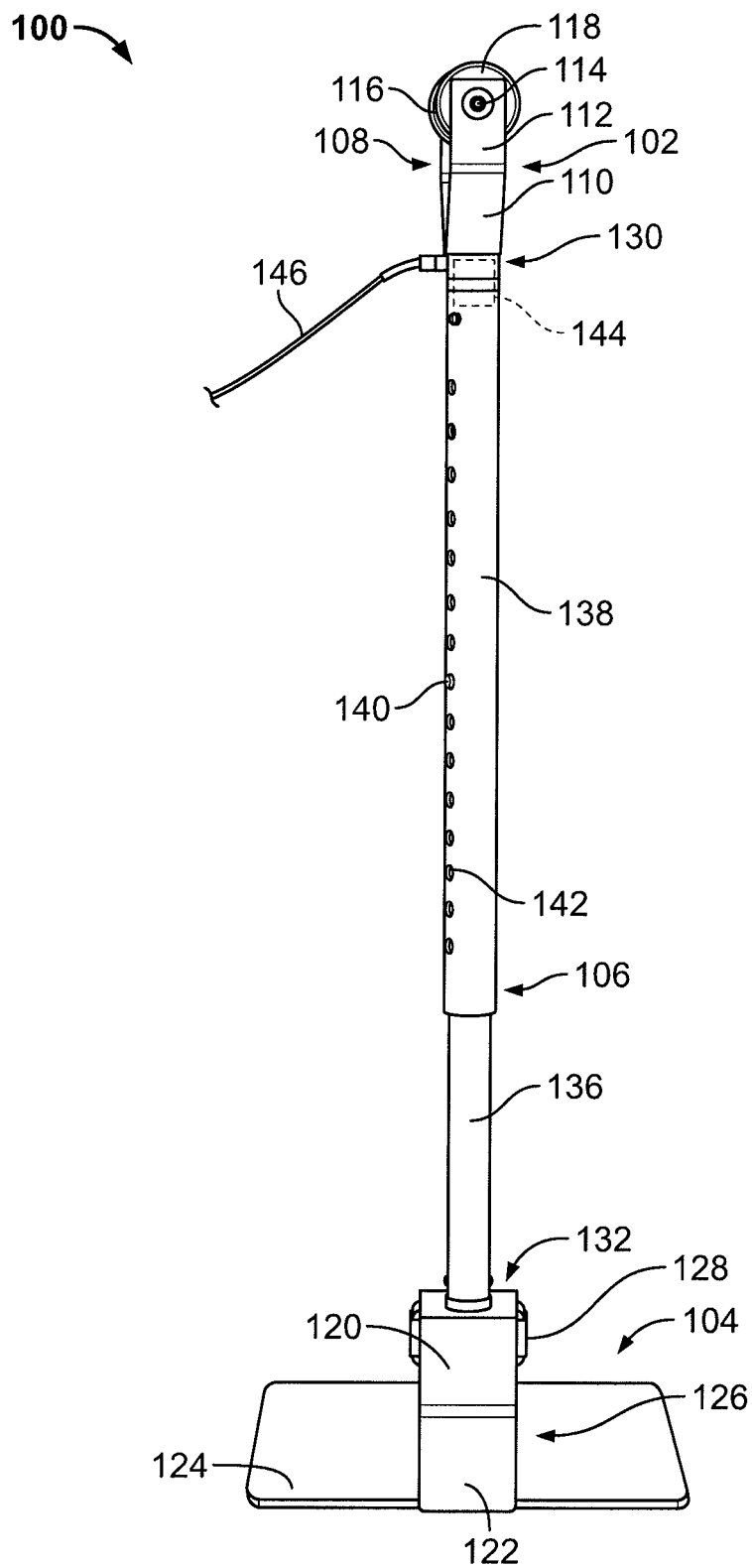
FIG. 3 is a side view of the exemplary muscle fatigue measuring device of FIG. 2.
Figure 4:
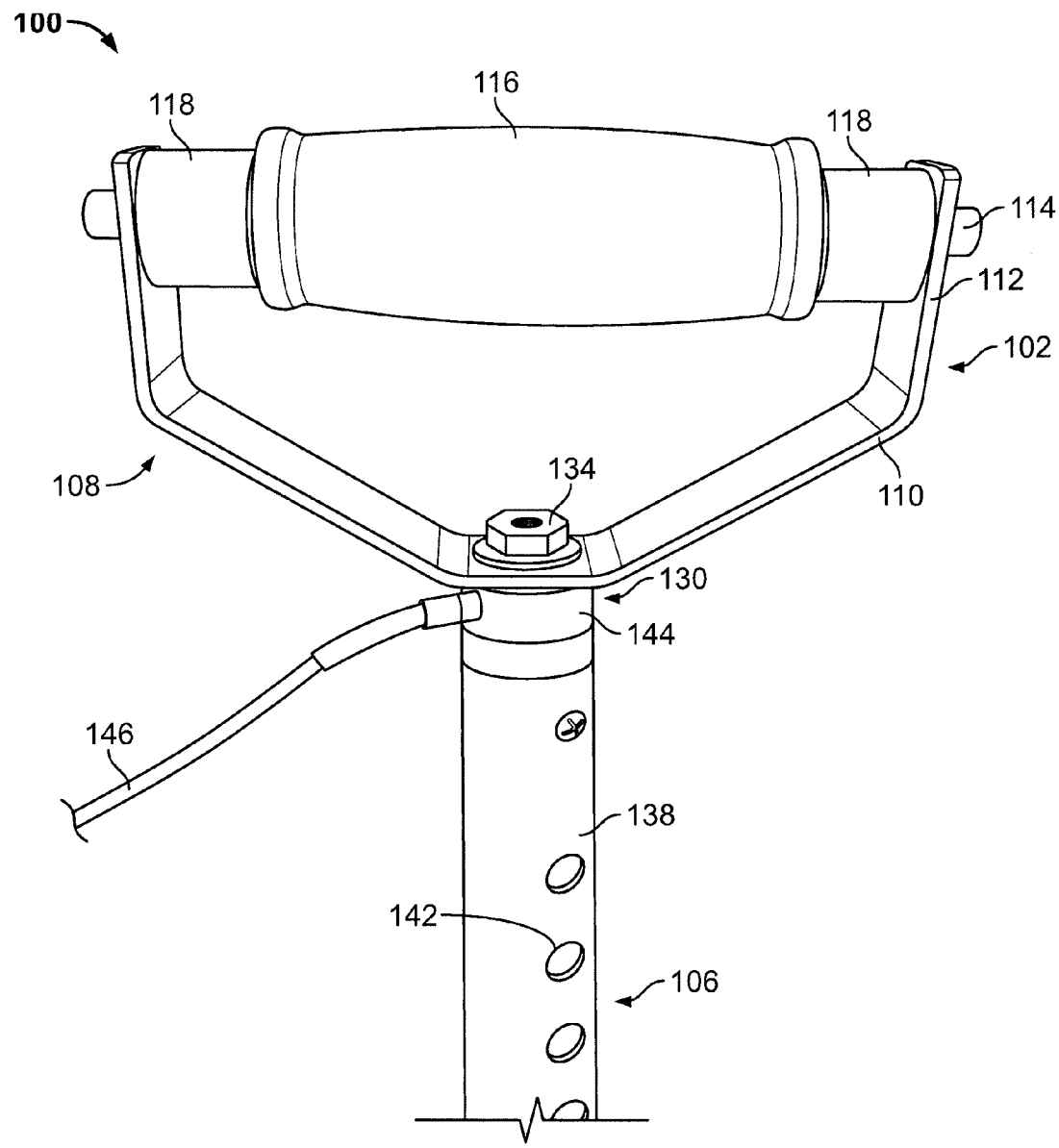
FIG. 4 is a detailed view of a handle of the exemplary muscle fatigue measuring device of FIG. 2.
Figure 5:
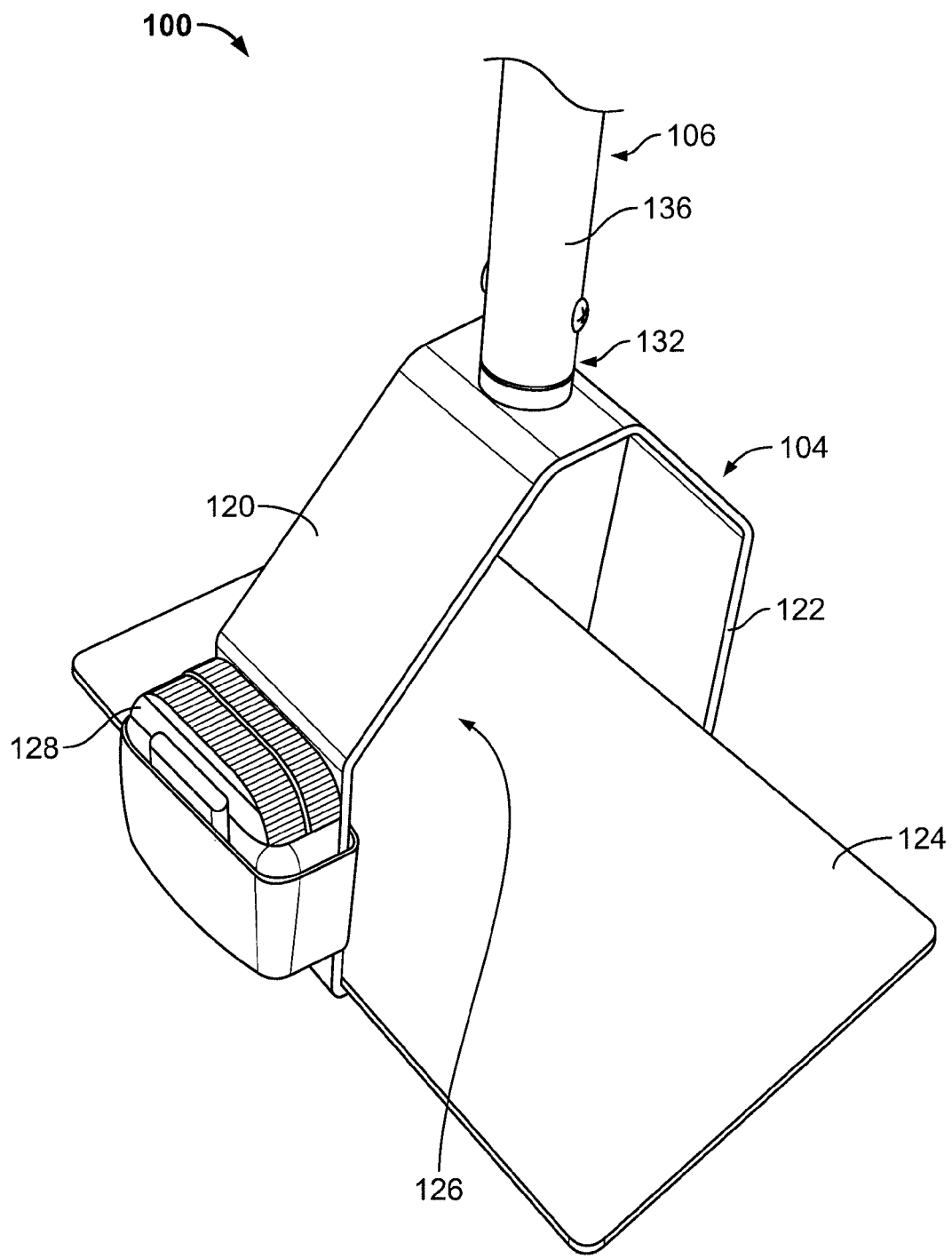
FIG. 5 is a detailed, perspective view of a bottom stabilizing portion of the exemplary muscle fatigue measuring device of FIG. 2.

In some embodiments, the base section 104 can include a stirrup for a foot of the user or another object to be placed inside to secure the base section 104. In some embodiments, the base section 104 can include one or more flanges to be pressed down upon to secure the base section 104. In some embodiments, the base section 104 can include one or more rings, bars, or both, external or inset, to be attached to another object that is secured to maintain the base section 104 secured during use of the device 100. Although a configuration of the base section 104 is shown in FIGS. 2, 3 and 5, it should be understood that alternative variations of the shape of the base section 104 are contemplated that may be effective in achieving one or more of the embodiments described herein.

The post section 106 defines an elongated member extending between the handle section 102 and the base section 104. In particular, the post section 106 includes a proximal end 130 and a distal end 132. The proximal end 130 can be secured to the handle section 102 and the distal end 132 can be secured to the base section 104. For example, the handle section 102 can be secured to the proximal end 130 of the post section 106 with a fixation device 134, e.g., a screw, a bolt, or the like. Although illustrated as substantially cylindrical in shape, in some embodiments, the post section 106 can define alternative configurations, e.g., square, rectangular, or the like. In some embodiments, the post section 106 can be tubular.

The post section 106 can be adjustable in height, e.g., length, such that the overall height of the device 100 can be adjusted or optimized based on the height of the user. For example, as will be described below, the height of the device 100 can be adjusted such that the handle section 102 is at approximately hip or waist level for the user. However, it should be understood that the height of the device 100 can be adjusted such that the handle section 102 is at other positions relative to the height of the user in order to isolate and measure muscle strength of other muscle groups.

The length of the post section 106 can vary depending on the size of the person, the size of the base section 104, the size of the handle section 102, combinations thereof, or the like. By adjusting the length of the post section 106, the height of the device 100 can be optimized to allow proper strength measurement of the muscles of interest. In particular, the adjusted height of the device 100 can be used such that the arm of the user is in the proper location for measuring forces on the isolated muscles of interest.

In some embodiments, the post section 106 can be telescoping. For example, the post section 106 can include a first post 136 (e.g., a first section) concentrically positioned within a second post 138 (e.g., a second section). The first post 136 can include one or more spring-loaded push buttons 140 and the second post 138 can include a plurality of spaced apertures 142 along the length of the second post 138. The apertures 142 can be configured and dimensioned to receive the push button 140 therein.

During use, the push button 140 can be depressed, the height of the post section 106 can be adjusted by sliding the second post 138 upward or downward relative to the first post 136, and the push button 140 can be released to enter the appropriate aperture 142 to lock the second post 138 in the desired height. Although illustrated as including a spring-loaded push button 140, in some embodiments, the post section 106 can include an alternative mechanism, e.g., a clevis pin, or the like, for securing the position of the first port 136 relative to the second post 138. In some embodiments, the height of the post section 106 can be varied by, e.g., pneumatic means, electric means, or the like. The height of the device 100 can thereby be adjusted within a range of approximately one foot to approximately five feet. For example, the size of the device 100 and the length of the post section 106 can be configured and dimensioned such that when the base section 104 is placed on the ground, the handle section 102, e.g., the grip 116, is positioned at the height of the person's hand when the arms are positioned at rest at the sides of the person, at waist height, at shoulder height, or any distance in between.

In some embodiments, the post section 106 can be flexible or rigid. In some embodiments, the post section 106 can be stretchable or non-stretchable. For example, in some embodiments, the post section 106 can be fabricated from a flexible tension wire which supports the handle section 102. A force imparted on the handle section 102 can thereby be measured at an angle of preference and not specifically in the vertical direction. The post section 106 can be fabricated from any material known to those of ordinary skill in the art. For example, the post section 106 can be fabricated from, e.g., metal, a chain, rubber, rope, fabric, plastic, a polymer, a composite, combinations thereof, or the like. However, it should be understood that alternative materials of fabrication can be used. The post section 106 can be designed to support a force of at least approximately 200 lbs.

The device 100 can include a force measuring device 144 disposed between the handle section 102 and the post section 106. In some embodiments, the force measuring device 144 can be disposed at least partially within the second post 138 of the post section 106. The force measuring device 144 can be a mechanical or electronic/digital device, e.g., a force gauge, a load cell, a force sensor, a sensor for measuring change in tension in a wire, or the like. However, it should be understood that alternative force measuring devices can be incorporated into the device 100.

The force measuring device 144 can be connected to the handle section 102 such that the force measuring device 144 can measure upward or vertical arc direction forces applied to the grip 116. In particular, the upward pulling force applied to the grip 116 can be substantially similar to the opposite movement of a throwing motion (see, e.g., the fifth and sixth phases 18, of FIG. 1) or starting a lawn mower. Depending on the circumstances, including the size of the person, the position of the device 100, and the lifting motion, the force can be applied to the grip 116 in a non-vertical direction. In some embodiments, the force measuring device 144 can measure the force applied to the grip 116 in a substantially upward or vertical direction, in a partially upward or vertical arc direction, or both. In some embodiments, the force measuring device 144 can be configured to sense only upward and vertical arc direction forces, and does not measure forces during rotation of the handle section 102 relative to the post section 106.

In some embodiments, the force measuring device 144 can be communicatively linked to a graphical user interface (GUI), e.g., a computer, a monitor, a gauge, or the like, which indicates the force applied on the grip 116 and measured by the force measuring device 144. In some embodiments, the GUI can include a mechanical gauge, an electronic/digital gauge, or both, indicating the measured force on the grip 116. In some embodiments, the force measuring device 144 can be communicatively linked to the GUI via, e.g., one or more wires 146, wirelessly, or the like. In some embodiments, a GUI can be incorporated into the device 100 such than an external GUI is not needed. For example, in some embodiments, the GUI can be located at or near the handle section 102, at or near the post section 106, or at or near the base section 104. Thus, upon applying an upwardly directed force on the grip 116, the GUI can provide the peak force measured or sensed by the force measuring device 144.

Figure 6:
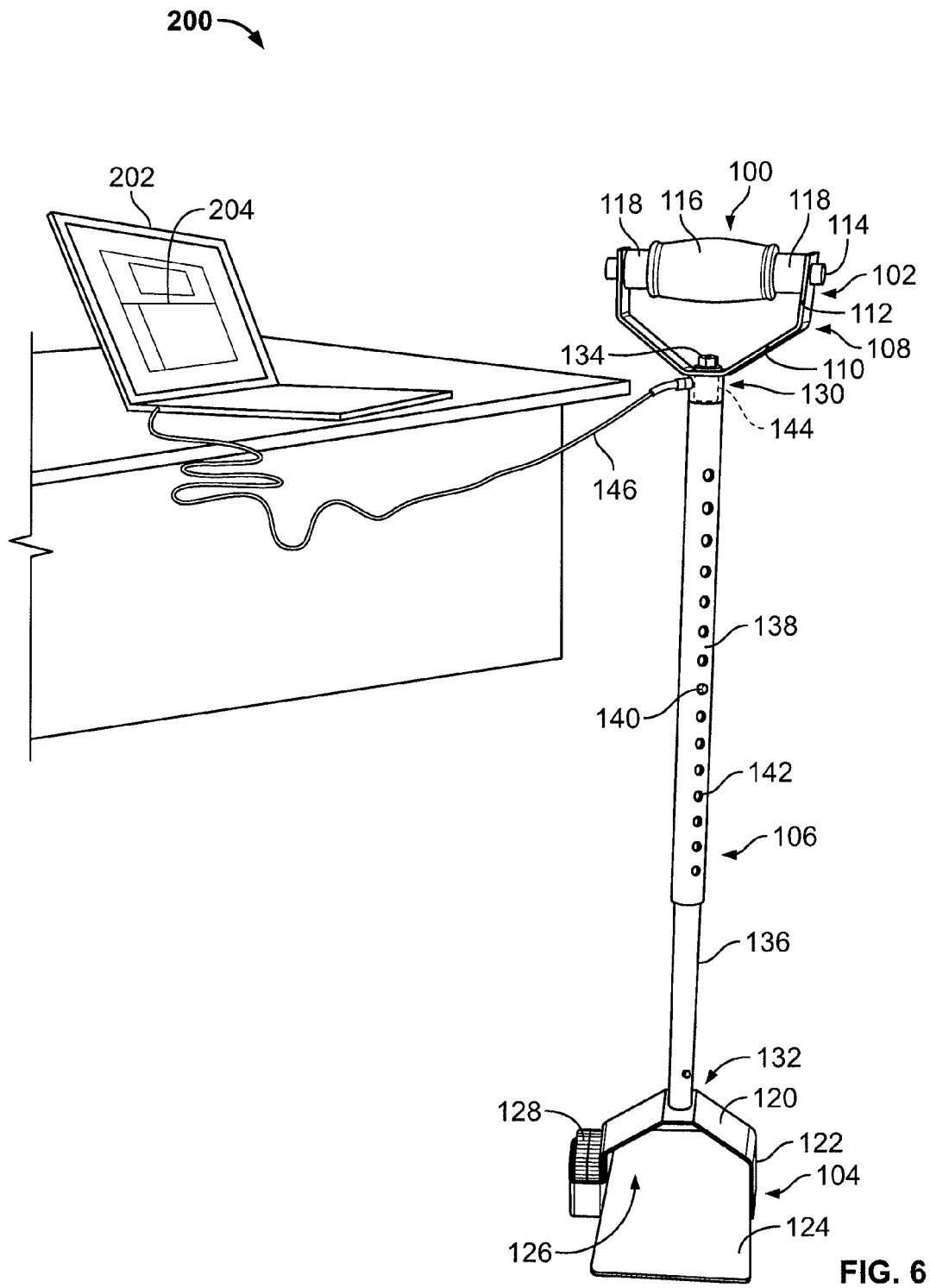
FIG. 6 is a perspective view of an exemplary muscle fatigue measuring system including the muscle fatigue measuring device of FIG. 2.

For example, FIG. 6 shows an exemplary muscle fatigue measuring system 200. The system 200 includes the device 100 and an external processing device 202, e.g., a computer. The processing device 202 can be connected to the device 100 via one or more wires 146 or wirelessly. The processing device 202 can include a graphical user interface (GUI) 204 which can record and output the force measured by the force measuring device 144 in a user friendly and readable manner. In some embodiments, the processing device 202 can include software and one or more storage devices programmed to store data values representative of measured forces for specific individuals such that force values measured over time can be compared relative to each other for the person to determine if muscle fatigue has occurred.

Figure 7:
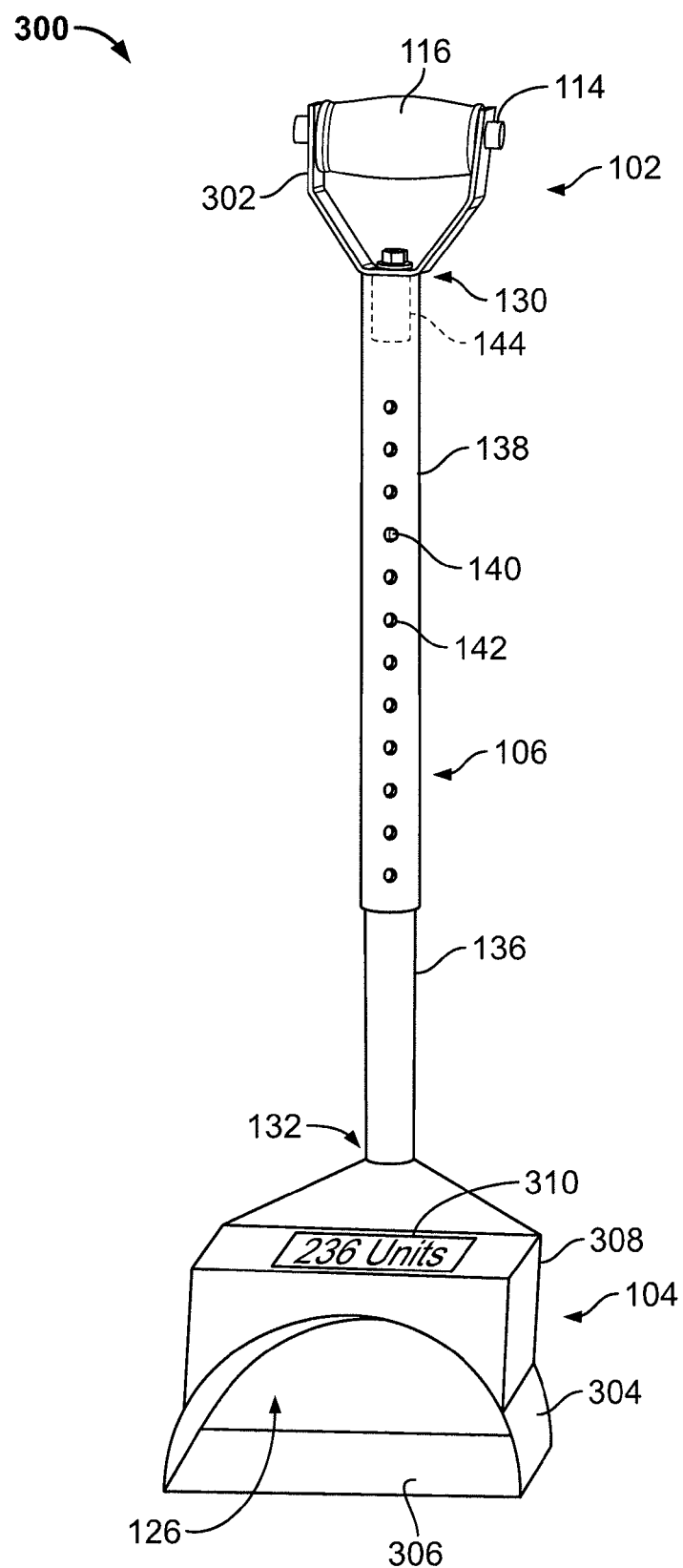
FIG. 7 is a perspective view of an exemplary muscle fatigue measuring device including a graphical user interface according to the present disclosure.

As a further example, FIG. 7 shows an exemplary muscle fatigue measuring device 300. The device 300 can be substantially similar in structure and function to the device 100 described above, except for the distinctions noted herein. Therefore, like reference numbers represent like structures. In particular, the device 100 includes a handle section 102, a base section 104, and an adjustable or telescoping post section 106.

The handle section 102 can include side members 302 extending from the post section 106 that define a rounded configuration. The grip 116 can be positioned between the spaced side members 302. The base section 104 can include rounded side members 304 and a bottom plate 306 which form a cavity 126 therebetween for introduction of at least a portion of the foot of the user. Rather than extending outward from the side members 304, the width of the bottom plate 306 can be dimensioned substantially similar to the width of the side members 304.

In some embodiments, a processing device 308 can be incorporated directly into the base section 104. The processing device 308 can be communicatively linked to the force measuring device 144 such that forces applied to the grip 116 can be displayed on a graphical user interface (GUI) 310. The GUI 310 can digitally or mechanically present the force measured by the force measuring device 144 to the user.

In some embodiments, the processing device 308 can include software and one or more storage devices programmed to store data values representative of measured forces for specific individuals such that force values measured over time can be compared relative to each other for the person to determine if muscle fatigue has occurred. In some embodiments, the processing device 308 can be configured to output the measured data to an external processing device (e.g., the processing device 202 of FIG. 6) such that the data can be analyzed.

The devices 100, 300 and associated systems 200 discussed herein can be used to measure the muscle fatigue in a person. A person can be positioned in a sitting or standing position and the height of the device 100, 300 can be adjusted by adjusting the height of the post section 106. The person can grasp the grip 116 with one hand and apply an upward force to the grip 116 to produce a measured force. In some embodiments, the distance measuring device 128 can be used to determine the position or stance of the person relative to the device 100, 300, thereby ensuring a consistent measurement of the desired muscles each time the device 100, 300 is used.

Figure 8:
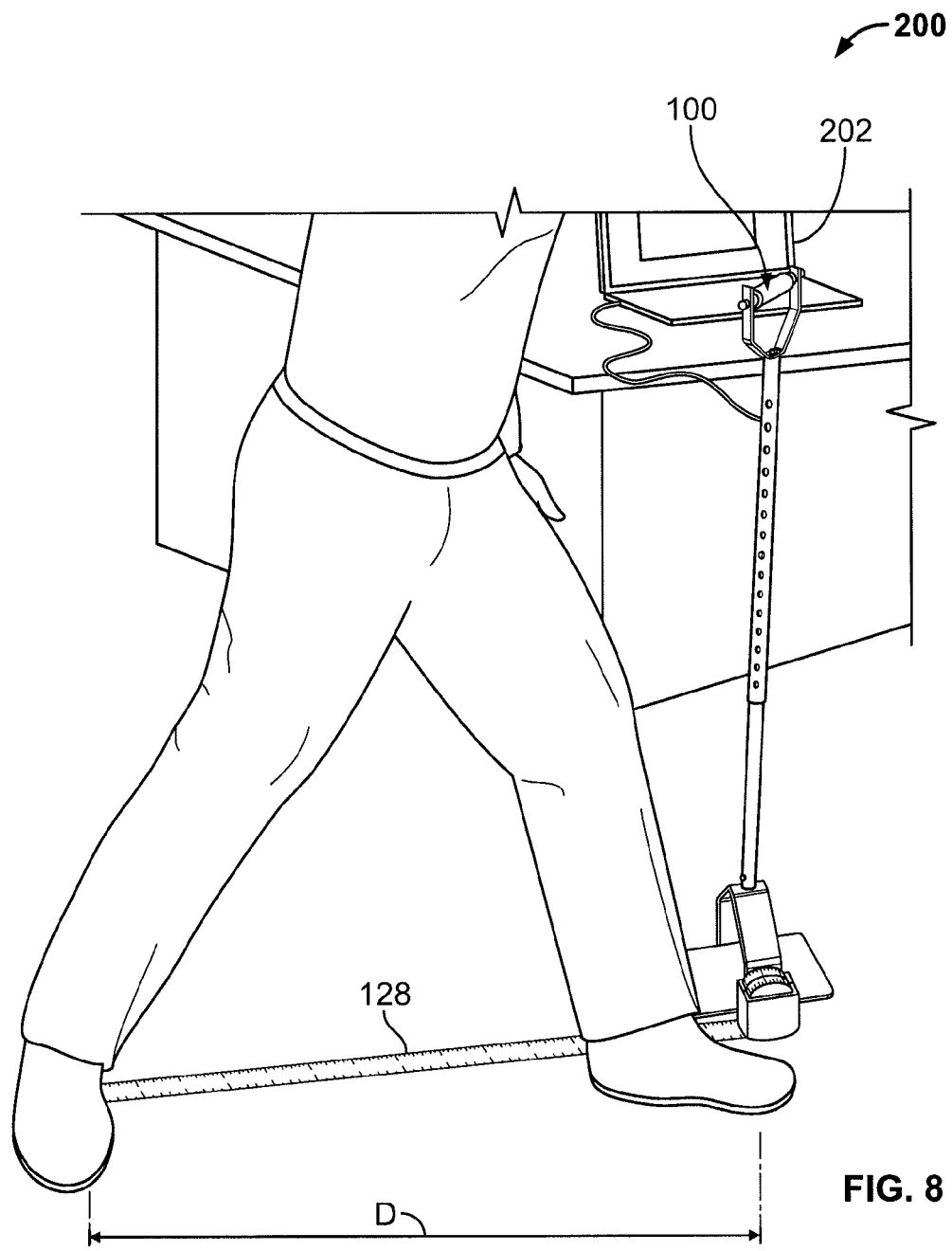
FIG. 8 is a side view of the exemplary muscle fatigue measuring device of FIG. 2 during measurement of a stride of a user.

For purposes of measuring fatigue of a baseball pitcher, as shown in FIG. 8, the pitcher can be asked to replicate the pitching motion and stop at the fourth or fifth phases 16, 18 (see FIG. 1). The distance D between the front and rear foot represents the stride of the pitcher. The distance measuring device 128 can be used to measure the distance D to ensure that the pitcher is standing at the proper position during use of the device 100.

Figure 9:
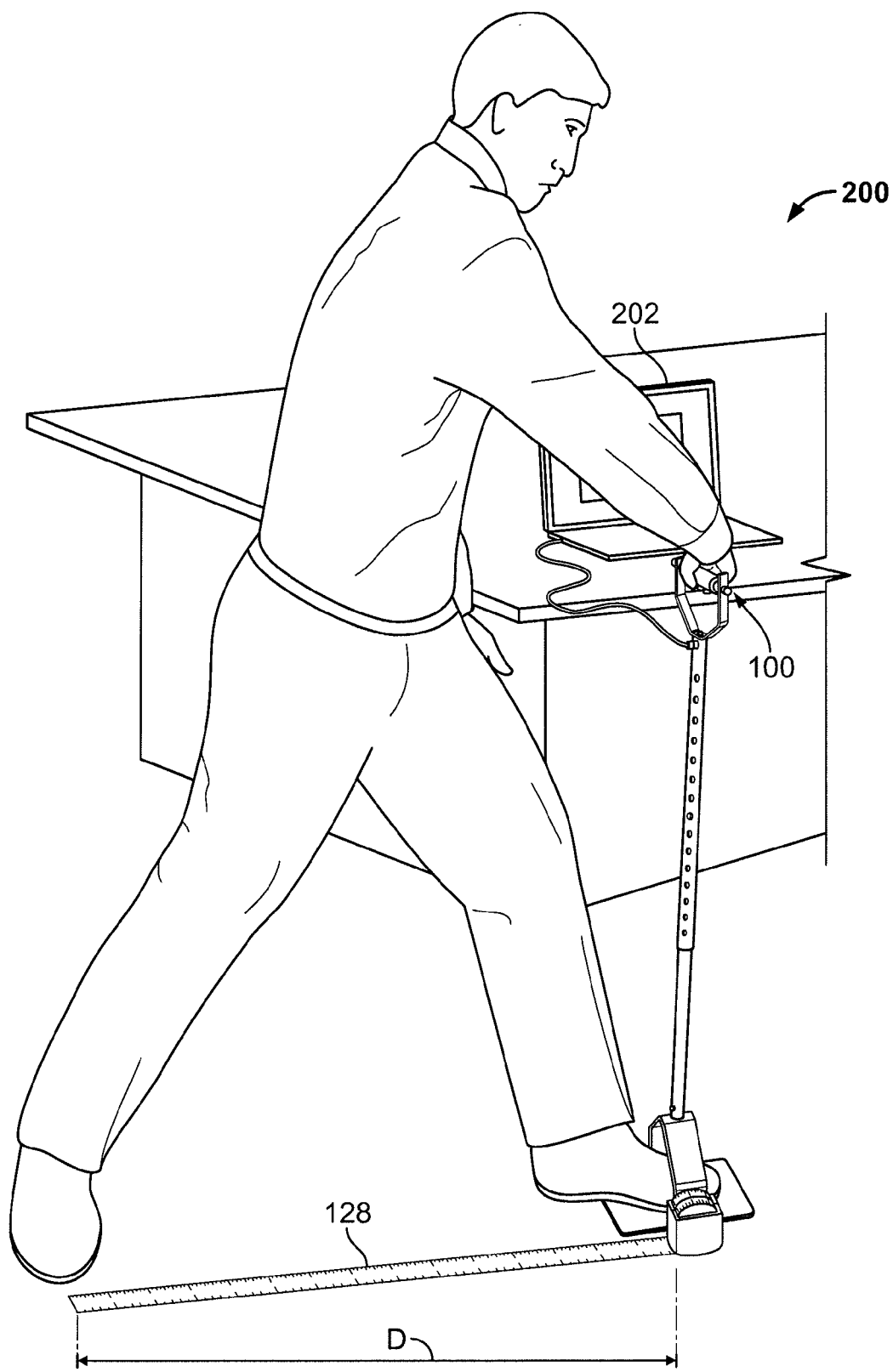
FIG. 9 is a side view of the exemplary muscle fatigue measuring device of FIG. 2 during measurement of muscle strength.

As shown in FIG. 9, with the stride distance D still shown by the distance measuring device 128, the pitcher can be asked to place the front or leading foot into the cavity 126 of the base section 104 while maintaining the rear foot at the distance D from the device 100. In particular, the pitcher's foot opposing the throwing arm can be placed in the base section 104. The pitcher's foot which matches the throwing arm can be offset behind the pitcher to resemble the position of the pitcher at the point of releasing the ball during a pitch. The height of the device 100 can be adjusted such that the handle section 102 is positioned at approximately waist level. The pitcher can stand erect and reach with the pitching arm extending in front of the body until the pitching hand reaches and grasps the grip 116. This position can be substantially similar to the position of the pitcher in the sixth phase 20 of the pitching motion (see FIG. 1).

The pitcher can further apply an upward force, e.g., an upwardly arced force, to the grip 116 to produce a measured force. The upwardly directed force on the grip 116 can represent the opposite motion of decelerating the pitching arm during the sixth and seventh phases 20, 22 of the pitching motion. By applying the upwardly directed force, the pitcher uses substantially similar muscles as used in the decelerating phases of the pitching motion. In particular, rather than measuring the eccentric forces of the muscles during the deceleration phase of the pitching motion, opposing and equivalent concentric forces of the muscles are measured. Fatigue of these muscles can therefore be measured and represents the substantially similar eccentric forces during the deceleration phase of the pitching motion.

Figure 10:
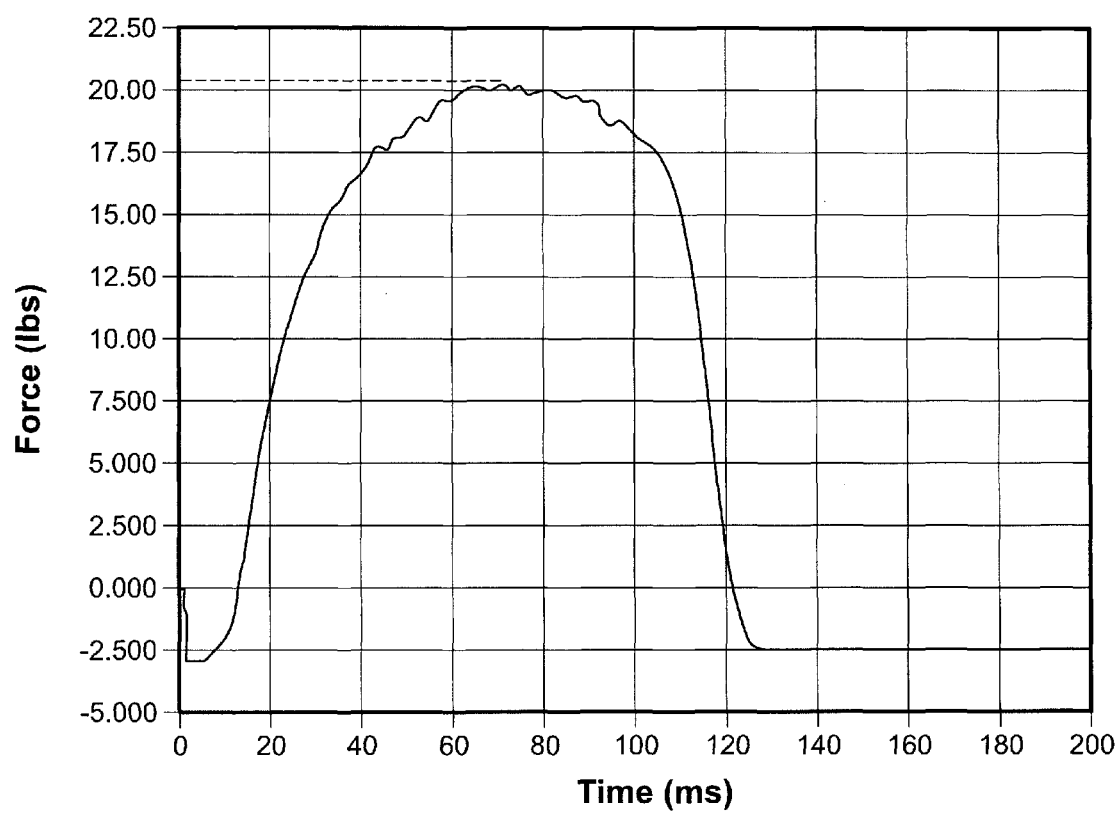
FIG. 10 is a chart of a muscle strength measurement from an exemplary muscle fatigue measuring system according to the present disclosure.

FIG. 10 shows a chart with an exemplary measured force as output by the device 100. In particular, at approximately 10 ms, the person begins applying an upward force on the grip 116 and at approximately 100 ms, the person releases the grip 116. The software associated with the device 100 can analyze the data and output the peak force measured, e.g., approximately 20 lbs. For example, the peak force can be measured before performing a task such that the peak force can represent the baseline value from which fatigue can be determined. In some embodiments, the peak force can be measured two or more times and an average can be used as the baseline peak force value.

Figure 11:
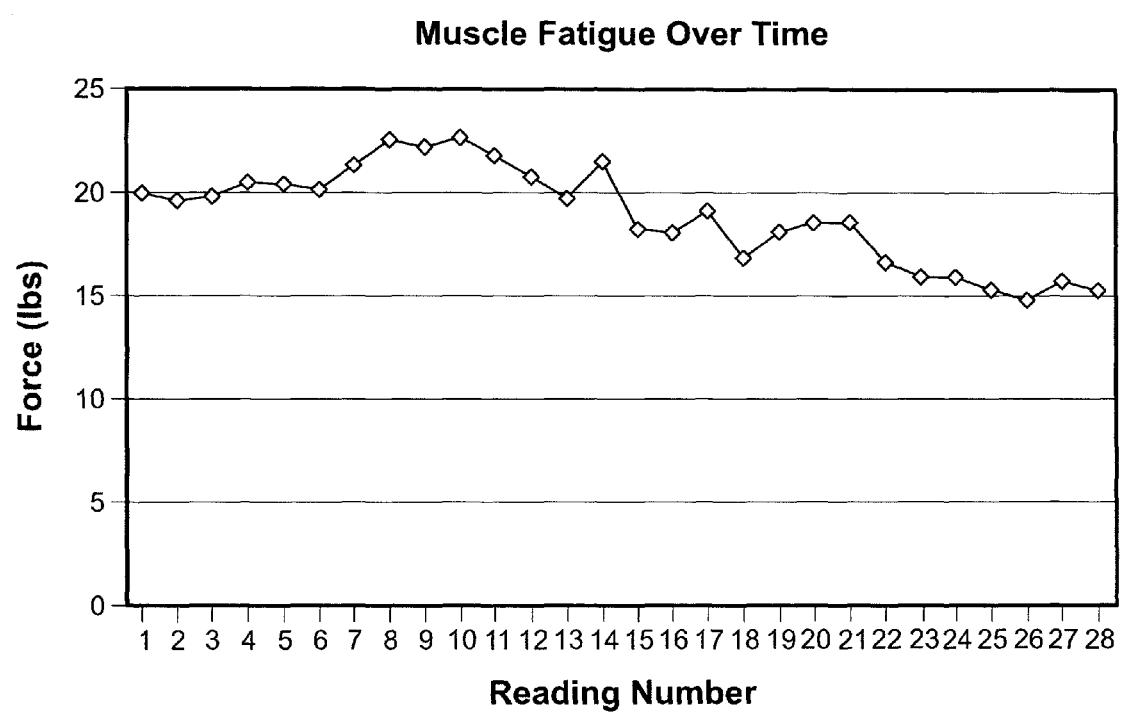
FIG. 11 is a chart of muscle fatigue over time from an exemplary muscle fatigue measuring system according to the present disclosure.

FIG. 11 shows a chart with exemplary measured forces over time as output by the device 100. The stride distance D of the pitcher was measured at approximately 48 inches and the height of the device 100 was adjusted such that the handle section 102 was at approximately 35 inches from the floor upon which the base section 104 was positioned. Twenty-eight force measurements were taken over a period of time to determine muscle fatigue of the pitcher. The data collected by the device 100 and shown in FIG. 11 is provided in Table 2 below.

TABLE 2

Muscle Fatigue Experimentation Data

| Reading Number | Force (lbs) |
| --- | --- |
| 1 | 19.96 |
| 2 | 19.63 |
| 3 | 19.83 |
| 4 | 20.47 |
| 5 | 20.45 |
| 6 | 20.17 |
| 7 | 21.37 |
| 8 | 22.57 |
| 9 | 22.21 |
| 10 | 22.67 |
| 11 | 21.83 |
| 12 | 20.76 |
| 13 | 19.77 |
| 14 | 21.49 |
| 15 | 18.27 |
| 16 | 18.12 |

TABLE 2-continued

Muscle Fatigue Experimentation Data

| Reading Number | Force (lbs) |
|---|---|
| 17 | 19.13 |
| 18 | 16.88 |
| 19 | 18.13 |
| 20 | 18.57 |
| 21 | 18.60 |
| 22 | 16.68 |
| 23 | 15.99 |
| 24 | 15.95 |
| 25 | 15.33 |
| 26 | 14.82 |
| 27 | 15.77 |
| 28 | 15.30 |

As can be seen from the data in Table 2 and the chart of FIG. 11, a warm-up phase occurred during reading numbers 1-9 with the measured force values gradually increasing. At reading number 10, the maximum measured force value is shown as approximately 22.67 lbs. The maximum measured force can be used as a baseline for a pitcher in determining at which point muscle fatigue has occurred and the task should be stopped to prevent potential injury. For example, the subsequent measured force values can be compared to a predetermined range or a percentage from the baseline value to determine if the measured values are beyond the fatigue point for the individual. Reading numbers 11-28 show a gradual decrease in the measured force value, indicating muscle fatigue over time. In particular, by reading number 28, an approximately 7 lb force reduction is shown as compared to the maximum measured force value.

As discussed above, the device 100 can be used to measure the muscle strength in one or more of the muscles in the arm and/or shoulder. In particular, what is measured is the amount of force applied to the device 100 when the user pulls or lifts the grip 116 in at least a substantially upward or vertical arc motion. The muscles responsible for the upward or vertical arc motion include, predominantly, the muscles of the arm and shoulder such as, for example the supraspinatus, infraspinatus, teres minor, and latisimus dorsi muscles. In one embodiment, these muscles are the muscles that are used to decelerate the arm when pitching a baseball.

The muscle strength can be monitored while performing a job or task. Before, during, and after the job or task, the muscle strength of the arm and/or shoulder muscles can be measured. The amount of muscle strength retained, or the amount of muscle fatigue, can be monitored. The measured force values can be monitored or evaluated to determine muscle fatigue generated during the job or task.

In some embodiments, the device 100 can be used to monitor the muscle strength, or fatigue, of a person performing the same job or task numerous times and correlating the muscle strength with the job performance and the potential risk of injury. For example, in the case of a baseball pitcher, the device 100 can be used to measure and monitor muscle fatigue at predetermined intervals during a baseball game, such as prior to the game beginning and then between innings. The value measured prior to the game beginning can be treated as a baseline value, e.g., a maximum force value, for the pitcher. A decline in the measure of a pitcher's muscle strength using the device 100 as compared to the baseline value can be correlated with performance decline and the potential risk of injury. As such, the device 100 can be used to monitor, determine and predict a pitcher's performance and potential injury.

In some embodiments, the fatigue point can be a predetermined muscle strength measurement, either point or range, that when approached, met or surpassed when performing the correlated job or task indicates an increased risk of potential injury to the arm and/or shoulder muscles if the job or task is continued without rest or recovery of the muscles. For example, upon reaching or closing in on a fatigue point, the pitcher can be asked to stop throwing pitches in the game. By stopping the pitcher from throwing any further pitches in a game, the health and stability of the arm and/or shoulder muscles are better protected with the intention that injury will be avoided. Upon regaining the muscle strength above the fatigue point, the pitcher can return to the game.

In some embodiments, the fatigue point can be calculated from past performance decline or injury history from the individual, or from statistical performance decline or injury from other similar individuals. For example, the fatigue point can be determined by gathering data over time using the device 100 for each individual. Currently, a baseball pitcher's arm fatigue is estimated based on performance and the number of pitches from previous performances. By measuring muscle function at regular intervals during a workout or a game, decline in muscle function can be determined with more precision and accuracy. As a result, poor performances and injuries can be reduced or prevented.

In some embodiments, a non-fatigued muscle strength measurement of a baseball pitcher can be determined before pitching in a baseball game. The non-fatigued measurement can be either measured before throwing warm-up pitches or after throwing warm up pitches. For example, by measuring the force value after the warm-up, the peak force value can be measured and stored as the baseline force value. In some embodiments, the fatigue point can be determined based on the measured force value dropping beyond a predetermined level. For example, if the peak force value is measured as 25 lbs, the fatigue point can be set at 15 lbs. If the force value drops to below 15 lbs after multiple innings, the pitcher can be asked to rest and removed from the game to prevent potential injury. The arm and/or shoulder muscles can thereby be sufficiently rested prior to additional pitching without undesired straining of the muscles.

In some embodiments, the baseline force value can be established over time with repetitive use of the device 100 such that cumulative fatigue or baseline weakness on a given day can be identified. For example, for a pitcher who has been rested for two days instead of the necessary four days, measurement and comparison of a force value with the device 100 can identify that the pitcher has not been sufficiently rested and the muscles are still fatigued. As a further example, if a pitcher is going through a period of time in which the muscles have not fully recovered from a previous stress, measurement and comparison of a force value with the device 100 can identify that the pitcher needs additional rest to recover beyond the baseline fatigue point. The pitcher can therefore be stopped from pitching, thereby allowing additional time for the arm and/or shoulder muscles to recover.

In some embodiments, the fatigue point of the pitcher can be a muscle strength measurement that is less than or equal to a percentage of the baseline value. For example, the fatigue point can be approximately 95% of the non-fatigued muscle strength measurement, e.g., the baseline value. Depending on the baseball pitcher, the fatigue point of the pitcher can be a muscle strength measurement that is less than or equal to approximately 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, or the like. In some embodiments, the fatigue point can be a range of percentages relative to the baseline value, such as approximately 94%-92%, 94%-90%, or the like.

It should be understood that the fatigue point associated with a heightened risk of injury and a decline in performance can be different for each baseball pitcher or individual. Therefore, customized values can be determined for a particular individual to determine at which point a fatigue point is reached. In some embodiments, based on data collected for a variety of individuals, a fatigue point value can be determined based on, e.g., age, size, baseline values, combinations thereof, or the like.

The device 100 can also be used to measure the amount of arm and/or shoulder muscle strength in the context of training, rehabilitation, or while performing a job or task. During training or rehabilitation, the muscle strength of the arm and/or shoulder can be measured on a scheduled basis, such as hourly, daily, weekly or at certain predetermined time points. The amount of muscle strength maintained or gained can be monitored. With respect to training or rehabilitation, the arm and/or shoulder muscle strength can be monitored to determine the effect or success of the training or rehabilitation exercises.

The force applied to the device 100 can be in any manner consistent with measuring the arm and/or shoulder muscle strength. In correlating different measurements, the manner used to measure the muscle strength or fatigue should be substantially consistent. In some embodiments, when measuring the muscle strength of a person's right shoulder, the person can stand in a pitcher's stance at the point of releasing the ball. Specifically, the user would be facing forward with the left foot forward and placed within the base section 104, the right foot extended back at the stride distance D, and the right arm extended forward out in front and over the left leg. With the arm extended, the right hand can grasp the grip 116 of the device 100 and pulls in an upwards arc for a force reading. In some embodiments, successive force readings can be taken using a substantially similar set-up and configuration. Alternative set-ups or configurations can include having the person in a sitting position, or alternatively standing with legs parallel to each other, with the arm extended out perpendicularly reaching towards the grip 116 of the device 100. Thus, the exemplary devices described herein can be used to measure and monitor muscle fatigue of a variety of users to prevent or reduce injury.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A muscle fatigue measuring device, comprising:
   a bottom stabilizing portion,
   a handle,
   a central extended portion disposed between the bottom stabilizing portion and the handle, and
   a force measuring device connected to the handle,
   wherein the bottom stabilizing portion is configured to receive a leading foot of a user and the handle is configured to be grasped by an opposing arm of the user, such positioning of the user isolating a force applied to the handle by a muscle selected from a supraspinatus muscle, an infraspinatus muscle, and a teres minor muscle of the user, and
   wherein the force measuring device is adapted to measure a first upwardly directed force applied to the handle to establish a baseline force value, and further adapted to measure a second upwardly directed force subsequently applied to the handle, a difference between the baseline force value and the measured second upwardly directed force indicating fatigue of the muscle selected from the supraspinatus muscle, the infraspinatus muscle, and the teres minor muscle of the user.

2. The muscle fatigue measuring device of claim 1, wherein the bottom stabilizing portion defines a base including a flat bottom plate adapted to be positioned on a supporting surface.

3. The muscle fatigue measuring device of claim 1, wherein the bottom stabilizing portion comprises a retractable distance measuring device attached thereto.

4. The muscle fatigue measuring device of claim 1, wherein the central extended portion comprises a post.

5. The muscle fatigue measuring device of claim 1, wherein a height of the central extended portion is adjustable.

6. The muscle fatigue measuring device of claim 1, wherein the central extended portion comprises a first section concentrically positioned within a second section in a telescoping manner.

7. The muscle fatigue measuring device of claim 6, wherein the first section comprises a spring-loaded push button.

8. The muscle fatigue measuring device of claim 7, wherein the second section comprises a plurality of apertures configured to receive the spring-loaded push button.

9. The muscle fatigue measuring device of claim 1, wherein the force measuring device is a load cell.

10. The muscle fatigue measuring device of claim 1, wherein the force measuring device is disposed between the handle and a proximal end of the central extended portion.

11. The muscle fatigue measuring device of claim 1, wherein the first upwardly directed force and the second upwardly directed force measured by the force measuring device is a force directed away from the bottom stabilizing portion and the central extended portion.

12. The muscle fatigue measuring device of claim 1, comprising a processing device and a graphical user interface secured to at least one of the handle, the central extended portion, or the bottom stabilizing portion.

13. The muscle fatigue measuring device of claim 12, wherein the graphical user interface displays the first upwardly directed force and the second upwardly directed force applied to the handle and measured by the force measuring device.

14. A method of measuring muscle fatigue, comprising:
   providing a muscle fatigue measuring device, the muscle fatigue measuring device including (i) a bottom stabilizing portion, (ii) a handle, (iii) a central extended portion disposed between the bottom stabilizing portion and the handle, and (iv) a force measuring device connected to the handle,
   introducing a leading foot of a user into the bottom stabilizing portion,
   grasping the handle with an opposing arm of the user, such positioning of the user isolating a force applied to the handle by a muscle selected from a supraspinatus muscle, an infraspinatus muscle, and a teres minor muscle of the user, applying a first upwardly directed force to the handle, measuring the first upwardly directed force applied to the handle with the force measuring device, establishing the measured first upwardly directed force as a baseline force value, applying a second upwardly directed force to the handle subsequently to the first upwardly directed force, measuring the second upwardly directed force applied to the handle with the force measuring device, and detecting fatigue of the muscle selected from the supraspinatus muscle, the infraspinatus muscle, and the teres minor muscle of the user based on a difference between the baseline force value and the measured second upwardly directed force.

15. The method of claim 14, comprising determining whether the measured second upwardly directed force is below a percentage of the baseline force value to determine if muscle fatigue is occurring.

16. The method of claim 14, comprising determining whether the measured second upwardly directed force is within a predetermined range of force values that signal muscle fatigue.

17. A muscle fatigue measuring system, comprising:
a muscle fatigue measuring device, the muscle fatigue measuring device including (i) a bottom stabilizing portion, (ii) a handle, (iii) a central extended portion disposed between the base and the handle, and (iv) a force measuring device connected to the handle, and a processing device connected to the force measuring device, wherein the bottom stabilizing portion is configured to receive a leading foot of a user and the handle is configured to be grasped by an opposing arm of the user, such positioning of the user isolating a force applied to the handle by a muscle selected from a supraspinatus muscle, an infraspinatus muscle, and a teres minor muscle of the user, wherein the force measuring device is adapted to measure a first upwardly directed force applied to the handle to establish a baseline force value, and further adapted to measure a second upwardly directed force subsequently applied to the handle, and wherein the processing device is adapted to receive as input and display the measured first upwardly directed force, display the baseline force value, receive as input and display the measured second upwardly directed force, and analyze the difference between the baseline force value and the measured second upwardly directed force to output fatigue of the muscle selected from the supraspinatus muscle, the infraspinatus muscle, and the teres minor muscle of the user.

18. The muscle fatigue measuring system of claim 17, wherein the processing device comprises a graphical user interface for displaying the measured first upwardly directed force, the measured second upwardly directed force, and the fatigue of the muscle selected from the supraspinatus muscle, the infraspinatus muscle, and the teres minor muscle of the user.

19. The muscle fatigue measuring device of claim 1, wherein:
the bottom stabilizing portion comprises vertical members and a bottom plate fixedly secured to the vertical members, the vertical members and the bottom plate forming a passage configured to receive a foot of a user, and the bottom plate extended anteriorly and posteriorly relative to the vertical members, the central extended portion defines a central longitudinal axis of the muscle fatigue measuring device, and the bottom stabilizing portion is aligned with the central longitudinal axis.

20. The muscle fatigue measuring device of claim 1, wherein the central extended portion is rigidly connected to the bottom stabilizing portion and the handle.

* * * * *